United States Patent [19]
Gueret et al.

[11] Patent Number: 5,026,552
[45] Date of Patent: Jun. 25, 1991

[54] SHEET MATERIAL FOR PERFORMING A SKIN OR HAIR TREATMENT, METHOD FOR ITS MANUFACTURE, AND ARTICLES MADE OF THIS MATERIAL

[75] Inventors: Jean-Louis Gueret, Paris; Jean-Claude Contamin, Morangis; Liliane Ayache, Paris, all of France

[73] Assignee: L'Oreal, Paris, France

[21] Appl. No.: 248,937

[22] Filed: Sep. 26, 1988

[30] Foreign Application Priority Data

Sep. 25, 1987 [FR] France ............... 87 13264

[51] Int. Cl.⁵ ............... A61K 6/00; A61K 7/06; A61K 31/74
[52] U.S. Cl. ............... 424/401; 424/70; 424/78; 424/402; 514/844; 428/255
[58] Field of Search ............... 424/401, 70, 78, 402; 428/255; 514/844

[56] References Cited

U.S. PATENT DOCUMENTS

| | | | |
|---|---|---|---|
| 3,428,043 | 2/1969 | Shepherd | 128/268 |
| 4,377,160 | 3/1983 | Romaine | 128/156 |
| 4,585,797 | 4/1986 | Cioca | 514/773 |
| 4,631,227 | 12/1986 | Nakamura | 428/283 |
| 4,643,939 | 2/1987 | Sugiyama et al. | 428/283 |

FOREIGN PATENT DOCUMENTS

WO8705206 9/1987 European Pat. Off.

*Primary Examiner*—Thurman K. Page
*Assistant Examiner*—G. S. Kishore
*Attorney, Agent, or Firm*—Cushman, Darby & Cushman

[57] ABSTRACT

The material according to the invention comprises a mesh (3) confining a hydratable gel (4) in a thin film is its holes. The gel is used for its properties of absorption of the water provided by a moistening of the surface of the skin; it is rehydrated at least partially and with the mesh resuming its natural flexibility molds to the irregularities of the body; then it dries under the influence of the normal skin temperature, the dry form being resumed while it continues to adhere to the skin. Because the gel is confined in its mesh, it can be pulled off all in one piece, so that the gel thereby performs a skin sloughing treatment.

8 Claims, 1 Drawing Sheet

SHEET MATERIAL FOR PERFORMING A SKIN OR HAIR TREATMENT, METHOD FOR ITS MANUFACTURE, AND ARTICLES MADE OF THIS MATERIAL

FIELD OF THE INVENTION

The present invention relates to a composite sheet material which is used by being applied temporarily to the skin surface or the scalp, for performing a localized skin or hair treatment, in particular for cosmetic purposes. The invention also relates to the manufacture of this material and to its manner of use.

BACKGROUND OF THE INVENTION

Depending on its structural characteristics, its composition and its form, the material according to the invention may comprise a mask intended for care of the face or a portion of the face (contouring of the eyes, cheeks, chin), in particular for deep cleaning of the skin by removing the horny layer of the epidermis, for firming the skin, for softening it, or subjecting the skin to a particular treatment; the material according to the invention may also comprise a useful element for firming the bust, or patches of the anti-wrinkle type for localized purposes. When applied to the scalp, the use of the material according to the invention can be used for hair conditioning treatments and for setting the hair, for example.

"Beauty mask" products are well known in the cosmetic field. They exist particularly in the form of gels or pastes, which dry, after being applied to the face, in order to produce a film that is removed by washing or cleaning or by being pulled off. During the drying period, the horny layer, or stratum corneum, becomes moistened and supple, and the skin contracts slightly. After drying, the blood flow is accelerated as a consequence of a rise in temperature. Moreover, the mask has an absorption effect, and when it is removed it thus assures deep cleaning of the skin at the same time as "peeling", in particular of the horny layer of the epidermis. European Patent Application No. 0 063 875 discloses a mask for the face comprising a sheet, suitably cut into the shape of the face, which serves as a vehicle for liquid cosmetic ingredients intended for transfer when the sheet is applied to the face.

French Patent Applications No. 2 512 651 and 2 538 247 also disclose anti-wrinkle patches that incorporate cosmetic or pharmaceutical substances in their material or in cavities therein. Once again, the treatment product is transferred directly to the skin.

Austrian Patent No. 206 114 described the beauty mask the shape of which corresponds to the anatomy of the face and which comprises a silk fabric impregnated with gel (polyvinyl alcohol) and covered with a layer of paste containing vegetable extracts and/or vitamins. The mask comprises two layers, and hence is thick, and must be remoistened just before use.

SUMMARY OF THE INVENTION

The present invention relates, among other subjects, to a new type of mask which is very convenient to use, since unlike the gels, pastes and sheets described above, it can be applied to the face in the dry state, after the face has been moistened, and can be lifted off quite easily, and in all cases, as with gels and pastes, it produces efficient cleansing of the pores of the skin by sloughing off the horny layer. Additionally, the mask according to the invention may contain active substances in the gel layer that make it possible to perform a complementary treatment by transfer of these substances to the skin.

The mask according to the invention comprises a mesh capturing a hydratable gel in a thin film in its holes. The gel is used for its properties of absorption of the water carried by moistening the surface of the skin; beginning in its slightly rigid dry form, it hydrates at least partially and becomes supple, the mesh then recovering its natural flexibility and molding to all the irregularities of the body (the socket of the eye, the hollow in wrinkles); then it dries under the influence of the normal temperature of the skin, the dry form being resumed while it is still adhering to the skin. Because the dry gel is always confined in its mesh, the system (mesh/gel) can be removed all in one piece, the gel having sloughed off the dead skin.

The use of a thin film of gel alone in combination with a reinforcing mesh has never been known until now. Moreover, the gel film was always applied in the moistened state to the skin.

Additionally, it is advantageous to benefit from the vehicle function of the gel, in order to produce at least one treatment product upon hydration of the gel and placement in contact with the skin.

Furthermore, it may be provided according to the invention that the impregnated mesh, cut to the dimensions of the part of the body to be treated, is applied to the body on the adhesive side of a sheet having an adhesive coating that is impermeable to water in the liquid or vapor state, so that the adhesive film is left uncovered by the mesh on the periphery of the sheet, in such a way as to create a patch, a mask, or more generally an occlusive element when it is glued to the skin. In this case, the water initially deposited into the skin hydrates the gel and dissolves the treatment substance, if any, that it contains; from then on, the treatment substance can be released, in order to act upon the skin. The water of perspiration does not pass through the mask because of the presence of the impermeable sheet, and upon condensing on the surface of the skin contributes to dissolving the active product; perspiration has the effect of opening the pores, which promotes the penetration of the active product. The transdermal phenomenon is accordingly activated. As a variant, if the support sheet has a certain permeability in the course of time, it may be possible to perform only a partial occlusion.

Hence the present invention relates first to an article for performing a local skin treatment or a hair conditioning treatment upon temporary application to the cutaneous surface or to the scalp, characterized in that it includes a flexible mesh that comprises the reinforcement for a thin film of hydratable gel.

The mesh is preferably made of a hydrophobic material, or in other words a non-absorbent material. Advantageously, a synthetic material such as polyamide is selected in preference to cotton, although cotton can certainly be used as well. It is also preferable for the mesh to be of a transparent material, because it is then possible, as applicable, to see when the application has been completed, by observing a change in color in the course of treatment, for example, through the transparent film. Additionally, transparent masks are more esthetically pleasing. It is also preferable to use a mesh made of material that can be sterilized at a high temperature. The use of polyamide meshes is particularly suitable. They make it possible to deposit a smaller quantity of gel, with quite good control being afforded by means of how thick the framework and the interstices formed by the holes of the mesh are.

The mesh may comprise a woven or nonwoven fabric having a thickness between 0.01 and 2 mm; counting approximately 2 to 100 holes per centimeter, the ratio between the surface area of its openings to the total surface area particularly being between 5 and 80%. Preferably a mesh of woven fabric is used, because nonwoven fabrics often contain binders which can promote the proliferation of microorganisms during storage or upon rehydration in the course of the application. Moreover, woven meshes mold better to the various shapes of the body than do nonwoven ones.

A mesh is also preferably used that is stretchable in only one direction. The reason for this choice has to do with manufacture of the article according to the invention; as will be described below, in industrial manufacture the mesh must be capable of being wound onto a reel and unwound from a reel without difficulty. A mesh that is stretchable in two directions would stretch while being wound.

The gel advantageously comprises a water-soluble or water-expandable polymer having a dry extract between 0.5 and 50% by weight. Polymers that can be used for this purpose are advantageously selected from the group including polyvinyl alcohol, alkaline metal salts of cross-linked carboxymethylcellulose, alkaline metal salts of polyacrylic acid, cross-linked polyalkylene oxide, alkaline metal salts of grafted acrylonitrile cellulose or acrylonitrile starch polymers containing carboxylic groups, gum tragacanth, gum arabic, guar gum and its derivatives, alginates, xanthan gum, other cellulose derivatives, albumin, gelatin, galactomannan and polyacrylamide.

The mesh, in the holes of which the gel is confined, makes it possible to use a very thin gel; without this reinforcement, such a thin gel would make a sheet that would not be strong enough to be handled. Now a very thin gel is necessary at the moment the mask (or the like) is applied, so that the mask can quickly absorb the moisture of the moistened treated part, in order to assure that the gel and hence the mesh/gel system will rapidly become supple, so that consequently the mask (or the like) can mold to the often sinuous shapes of the portions of the face or body being treated, and finally so that rapid evaporation of the reabsorbed water will take place, so as to re-dry the gel, in the case where the mask is not occlusive. The mean thickness of gel on the mesh will typically be between 5 and 1000 μm.

Moreover, the gel can advantageously include at least one active treatment substance, particularly for cosmetic purposes, selected particularly from among the following substances: water-soluble active agents, clay, kaolin, silica, emulsified oils, moisturizing agents, thinners, anti-wrinkle agents, stimulants, revitalizers, firming agents, and softeners, powders, and the like. In this case, it is particularly important for the mean thickness of the gel on the mesh to be low. In fact, when the thickness of the gel layer is excessively high, it is very difficult to moisten this layer suitably, and even if the mask becomes sufficiently supple, the non-rehydrated layer absorbs water and prevents the active substances from remaining in contact with the portion of the body being treated.

When the mask includes at least two active substances, it can be provided that these active substances are located at different sites on the mesh. This possibility is advantageously used when the active products are not compatible with one another. In that case, the gel surface that will be applied to the skin can be moistened immediately prior to application, for example with the aid of a bottle provided with a stopper, with an aqueous or hydroalcoholic solution containing the active substances that are not compatible with those contained in the dry gel.

The material according to the invention may be used to make an article which advantageously has a cut shape adapted to the shape of the body part to be treated.

In particular, in the case of a mask intended for treatment of the face, it can be provided that this mask is made in two parts, one corresponding to the forehead and extending along its lower edge between two curved cuts that follow the contour of the eyebrow arch and along a flap intended to cover the skin of the nose, and the other part corresponding to the region of the face located below the eyes and including two openings respectively corresponding to the mouth and the nose, the upper edge of this part of the mask including two curved cuts intended for following the lower line of the eyes. These two-piece masks adjust well to different face shapes.

In another possible embodiment of a mask intended for treatment of the face, the mask comprises a single piece, cut in the shape and to the dimension of the face, this piece including openings corresponding to the eyes and the mouth, respectively, as well as a cut corresponding to the middle and lower region of the nose and freeing a flap intended to cover the nose; a median window connects the opening corresponding to the mouth and this cut, and transverse windows are also made along the lateral edges of this piece.

Additionally, according to the invention, elements can be provided for firming the bust, including a cutout substantially in the shape of half a ring.

According to the invention, the impregnated mesh can be supported on one of its surfaces by a protective detachable support sheet, and as applicable can be protected on its other side by another detachable protective sheet. In the case of masks that are totally or partially occlusive, the gel-impregnated mesh, cut to the dimension corresponding to the part of the body to be treated is disposed on the adhesive side of a support sheet (which is either impermeable or has a partial permeability, if the mask is partially occlusive) coated with a layer of adhesive on one of its sides, the sheet extending beyond the gel-impregnated mesh over its entire circumference, and a detachable backing protecting at least the adhesive portion prior to use. It may also be provided that a plurality of impregnated mesh elements, each including a different active substance, are disposed separately on the same support sheet.

In addition, whether or nor the mask according to the invention is occlusive, at least one zone of mesh impregnated with the gel can be provided that is partially or totally impermeable because of a fraction of the support sheet of limited surface area.

The material according to the invention could also be associated with a spongy material saturated with at least one treatment substance that is not compatible over time with the gel and/or with the substance or substances for continuous treatment, as applicable, in the gel.

The present invention also relates to a method of manufacture of a material according to the invention including a support sheet, this method being characterized in that:

a ply comprising a flexible mesh is placed on a support sheet capable of resisting the heating temperature of the hydrated gel in the later drying step;

a thin film of a hydrated gel, in a liquid or extrudable state and optionally including at least one active treatment substance is disposed on the thus-supported ply in such a manner as to fill the holes of the mesh comprising the ply with the hydrated gel;

the hydrated gel is dried until the degree of dehydration desired is obtained.

In order then to make an article of the thus-manufactured material, the material is cut in an appropriate manner and packaged for the intended use.

The coating with the hydrated gel can be performed by calendering or by extrusion.

The drying of the hydrated gel confined in the holes can be performed by calendering or by causing the mesh to pass through an infrared tunnel or blowing hot air onto it; a protective backing may be placed on the supported mesh, in the case where the calendering is done.

The invention also relates to the use of the above-defined material for a cosmetic skin treatment or hair conditioning, in which after the part of the body to be treated, or the scalp, has been moistened, the mesh impregnated with the hydratable gel is applied, integrally with its support sheet in the case where an at least partially occlusive treatment is performed; the application is continued for a time sufficient to assure drying of the gel that was rehydrated by contact with the moistened region; and the mesh is removed by being pulled off all in one piece.

So that the subject of the present invention will be better understood, an exemplary embodiment of the method of manufacture of a gel-impregnated mesh according to the invention will now be described, as well as several embodiments of articles made of this impregnated mesh, the embodiments described herein and shown in the accompanying drawings serving solely as illustrative and non-limiting examples.

DESCRIPTION OF THE PREFERRED EMBODIMENTS

Figure 1:
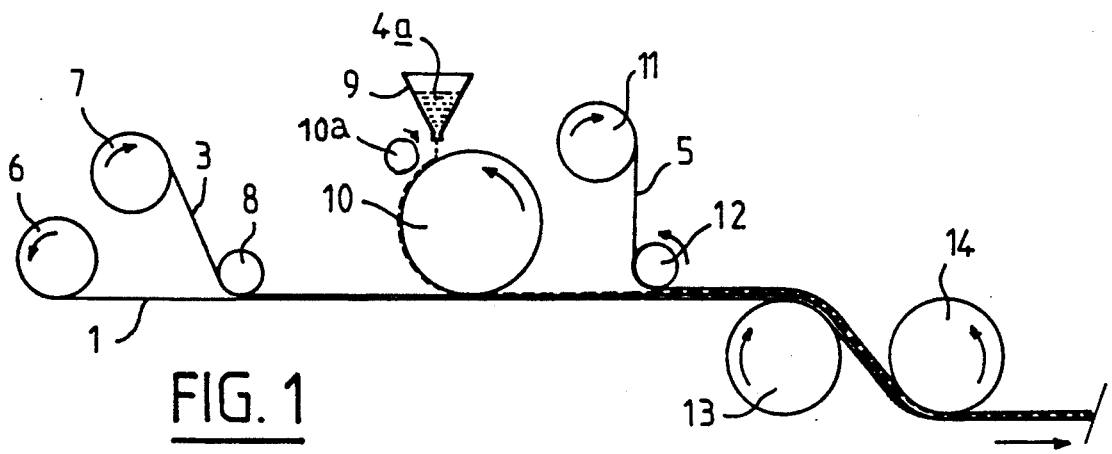
FIG. 1 is a diagram of the entire assembly, illustrating one embodiment of the method according to the invention.
Figure 2A:
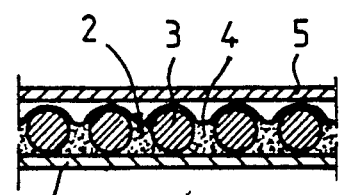
FIGS. 2A and 2B are sectional views on an enlarged scale of the composite material obtained by performing the method schematically illustrated by FIG. 1, these two materials differing from one another in the quantity of gel applied to the mesh.
Figure 2B:
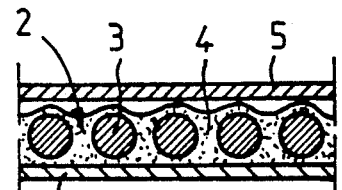

In FIG. 1, the apparatus required for manufacturing the composite material as shown in FIGS. 2A and 2B is schematically shown. This material includes three superimposed layers, that is, a support sheet 1 of polyester, polyethylene, or silicone-coated paper, which makes it possible to glaze the gel surface to be applied to the skin and which has good temperature resistance, a material 2, comprising a ply embodied by a polyamide mesh 3, between the holes of which an at least partially dehydrated gel 4 is confined and an upper protective sheet 5. A polyester sheet 1 wound on a reel 6 is unwound from the reel and is made to travel horizontally. A ply comprising the mesh 3 is then applied to the unwound sheet 1, the mesh 3 being unwound from its reel 7 and passing beneath a cylinder 8 disposed just below the sheet 1, in order to apply the mesh 3 to the sheet 1.

Downstream from the cylinder 8, a hydrated gel 4a in the fluid state, contained in a hopper 9, is applied to the traveling mesh 3 resting on the sheet 1. The hopper 3 includes an elongated window at its lower edge, by way of which the hydrated gel 4a drains in the form of a curtain that falls onto an applicator drum 10; a second drum 10a at an adjustable distance serves to spread the hydrated gel 4a; the drums 10, 10a have an axis perpendicular to the direction of forward motion of the ply on its support, and the drum 10 rolls on the mesh 3 in such a way as to apply a thin film of gel 4a. Downstream of the applicator drum 10, a second sheet 5, of polyester, which unwinds from a reel 11, is applied to the gel-filled mesh 3 with the aid of a roller 12.

The thus-formed composite material first passes over a first heated calender roller 13 and then beneath a second calender cylinder 14, the outer sheets 1 and 5 serving to protect the gel in the course of dehydration on the mesh when it passes vertically between the cylinders 13 and 14.

Depending on the spacing of the drums 10, 10a, gel is more or less spread out, and a mesh 3 more or less filled with gel is obtained, as shown in FIGS. 2A and 2B. FIG. 2B illustrates the case where the mesh is embedded completely in the gel. The choice of the quantity of gels depends on the particular use intended.

After manufacture, the sheets 1 and 3 are removed, if desired; it may be preferable to retain the sheet 1, for packaging of a mask after it has been cut out.

Figure 3:
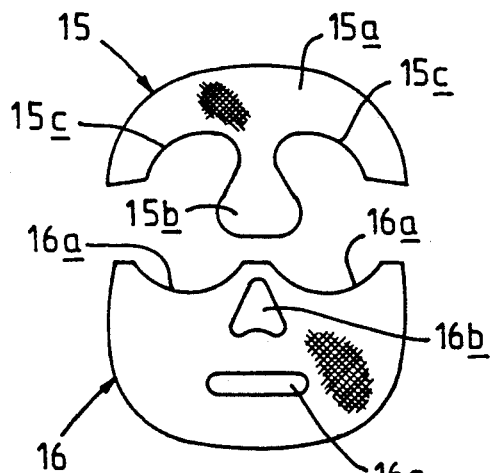
FIG. 3 is a plan view of a mask for the face, made in two pieces, which has been cut from a composite material according to the invention.
Figure 4:
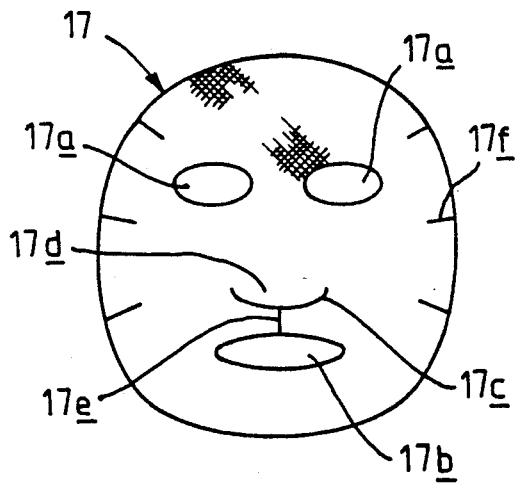
FIG. 4 is a view similar to FIG. 3 of a mask made in a single piece.
Figure 5:
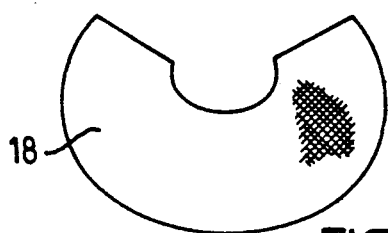
FIG. 5 is a plan view of an article according to the invention intended for firming the bust.

For the various usages, the material 2 obtained is then cut. FIGS. 3-5 illustrate various possible ways of cutting it.

In FIG. 3, a mask for the face has been provided that is made in two parts. The upper part 15 comprises a main strip 15a in the form of a ring, for molding to the forehead, and it is extended along its lower edge, in the middle region, by a tongue 15b intended for covering the nose. This tongue, which flares out toward its free end, is thus located between two curved cuts 15c that mold to the shape of the eyebrow arches. The remaining part 16 is intended for covering the face, in the region located under the midline of the eyes. To this end, it has a rounded shape in its lower portion in order to mold to the oval of the face; the upper edge includes two curved cuts 16a intended to follow the lower line of each eye. Two openings, 16b and 16c respectively, are also provided for the passage of the nose and mouth through them. This mask is made in two parts, to take into account the sphericity of the face; moreover, it has the advantage of being adjustable in height depending on the structure of the face.

The choice may instead be a mask of the type shown in FIG. 4. In this case, it is made is one piece, with two openings 17a provided for the eyes and one opening 17b provided for the mouth. A curved cut 17c is also provided above the opening 17b, this curved cut forming a flap 17d intended for covering the nose. The cut 17c and the opening 17b are joined by a window 17e, to facilitate application of the mask. Similarly, at least one window 17f is formed in each side edge, for the sake of better-adjusted emplacement of the mask, taking into account the sphericity of the face.

The gel 4 may contain active substances in mixture with it and distributed uniformly throughout the gel. An application of different gels, each including a different active substance, may also be provided on the same mesh, at different sites on the mesh, for example in parallel lines or strips.

By way of example, a material 2 according to the invention can now be described somewhat more precisely. The mesh 3 may be a netlike fabric including 85 holes per centimeter and made with polyamide threads 150 μm in diameter; it is filled with a polyvinyl alcohol which is spread by the drum, from 10 to 30% by weight of dry extract and dried to 98% by weight of dry extract. This material 2 includes 0.03 g/cm² of gel after drying.

The manner in which the masks that have just been described act upon the face, which is entirely novel and original, will now be described. First, the user detaches the mask itself, that is, the material 2, from the support sheet 1; the user then applies it to his face, which he has moistened beforehand, for example using a sponge.

The mask, once it is applied, loses its stiffness because the gel rehydrates in contact with the moistened skin. Under these conditions, the mesh resumes its supple and flexible nature and is immediately deformable, which enables it to mold to all the irregularities of the face.

The mesh now adheres to the skin, initially in the form of moisture contact, and then in the form of a dry adhesive. Within about 5 to 10 minutes, the gel, which has been rehydrated with the water with which the skin was moistened, dries in air, depending on the specific temperature of the skin. The gel, still confined by the mesh, thus becomes removable all in one piece, the gel having in the conventional manner effected a peeling of the skin.

When the gel includes at least one treating, thinning, anti-wrinkle or moisturizing substance, the gel has served as a vehicle for this substance from the moment when the bond between the gel and the skin was made. In this case, it may be desirable for the masks to be worn for an entire night, for intra-dermal treatment. The gels used are perfectly compatible with the skin and are harmless. In the case where active substances not compatible over time with the gel and the active substances it may contain are desired to be applied, these substances are applied with the water that moistens the skin. In this case, one may optionally perform rapid moisturizing, for example with the aid of a bottle provided with a stopper; the surface of the gel that will be applied to the skin with an aqueous or hydroalcoholic solution contains the active substances that are not compatible with those contained in the dry gel.

FIG. 5 shows an element 18 that can be used for firming the bust. This element is in the form of a half-ring, and the manner in which it is applied and functions are identical to those described above.

Figure 6:
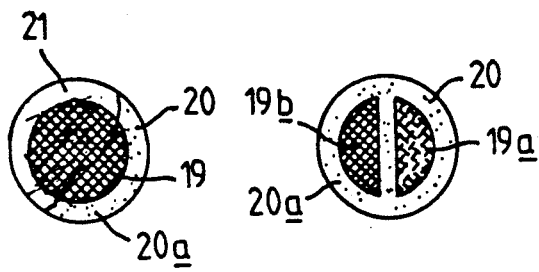
FIG. 6 is a schematic view illustrating the embodiment of an occlusive patch with a material according to the invention.

FIG. 6 is a drawing showing another possibility of the invention, in which the material 2 includes a gel which for example includes an anti-wrinkle substance; it is cut to a desired shape (for simplification, a patch 19 has been shown in FIG. 6) and is applied to the adhesive film 20a covering one surface of a support sheet 20 that is impermeable to water in the liquid or vapor state, such that the adhesive region is left free at the periphery of the sheet 20, being protected for packaging by a detachable sheet 21, for example a silicon-coated sheet.

For use, the patch 19 is applied with its support sheet 20, the positioning adhesive 20a causing occlusion at the periphery; the water deposited on the skin rehydrates the gel, which as applicable releases the active substance. In any case, because of the impermeability of the sheet 20, the water of perspiration does not evaporate, and it is used for rediluting the substance, which can then better penetrate the pores, which open increasingly because of the occlusion, which is total or partial depending on the material selected for making the sheet 20.

Figure 7:
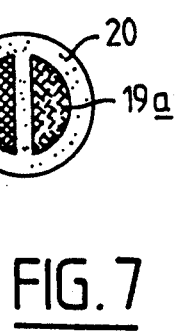
FIG. 7 is a schematic view of a variant embodiment of the occlusive patch of FIG. 6.

FIG. 7 shows a variant of the element of FIG. 6, in which the patch 19 is replaced with two pieces 19a, 19b, in which the dehydrated gel includes different active substances not compatible with one another over time; these pieces each are substantially in the shape of half of a disk and are thus separated by an interval on the support sheet 20. The manner of action is identical to that of the element of FIG. 6; the active substances cannot come into contact with one another except upon their release.

It will be understood that the embodiments described above are in no way limiting and can be modified in any way desirable, without departing from the scope of the invention.

What is claimed is:

1. A dry sheet for performing a local skin treatment or hair conditioning treatment upon temporary application in a dry state to a wet cutaneous surface or scalp, said sheet which is a flexible mesh made out of a fabric having a thickness between 0.01 and 2 mm with between approximately 2 to 100 holes per centimeter, the ratio between the surface area of said holes to the total surface area of said sheet being between 5 and 80% and a film of hydratable polymer gel being coated on said mesh and said gel having a mean thickness ranging between 5 and 100 μm.

2. A material as defined by claim 1, characterized in that the mesh (3) is made of a hydrophobic material.

3. A material as defined by claim 1 or 2, characterized in that the mesh is made of a transparent material.

4. A material as defined by one of the claim 1, characterized in that the mesh is made of material that can be sterilized at a high temperature.

5. A material as defined by one of the claim 1, characterized in that the mesh is of polyamide.

6. A material as defined by claim 1, characterized in that the mesh is a mesh that is stretchable in only one direction.

7. A material as defined by claim 6, characterized in that the gel (4) comprises at least one water-soluble or water-expandable polymer having a dry extract between 0.5 and 50% by weight 8. A material as defined by claim 7, characterized in that the gel includes a polymer selected from the group including polyvinyl alcohol, alkaline metal salts of cross-linked carboxymethylcellulose, alkaline metal salts of polyacrylic acid, cross-linked polyalkylene oxide, alkaline metal salts of grafted acrylonitrile cellulose or acrylonitrile starch polymers containing carboxylic groups, gum tragacanth, gum arabic, guar gum and its derivatives, alginates, xanthan gum, other cellulose derivatives, albumin, gelatin, galactomannan and polyacrylamide.

* * * * *

UNITED STATES PATENT AND TRADEMARK OFFICE
CERTIFICATE OF CORRECTION

PATENT NO. : 5,026,552
DATED : June 25, 1991
INVENTOR(S) : Jean-Louis Gueret, Jean-Claude Contamin, Liliane Ayache It is certified that error appears in the above-indentified patent and that said Letters Patent is hereby corrected as shown below:

In claim 1, column 8, line 49, "between 5 and 100 $\mu$m" should read -- between 5 and 1000 $\mu$m --.

Signed and Sealed this

Sixteenth Day of June, 1998

Attest:

BRUCE LEHMAN

*Attesting Officer*   *Commissioner of Patents and Trademarks*